United States Patent [19]

Mark et al.

[11] 4,358,624

[45] Nov. 9, 1982

[54] FLUORINATED MONOPHENOLS AND DIPHENOLS AND METHOD FOR THEIR PREPARATION

[75] Inventors: Victor Mark, Evansville; Charles V. Hedges, Mount Vernon, both of Ind.

[73] Assignee: General Electric Company, Mt. Vernon, Ind.

[21] Appl. No.: 221,703

[22] Filed: Dec. 31, 1980

[51] Int. Cl.$^3$ .............................................. C07C 39/14
[52] U.S. Cl. .................................. 568/722; 568/726; 568/715; 568/811
[58] Field of Search ............... 568/726, 774, 775, 715, 568/811, 765, 764, 722

[56] References Cited

U.S. PATENT DOCUMENTS

| | | | |
|---|---|---|---|
| 2,435,014 | 1/1948 | Niederl | 260/619 |
| 3,028,365 | 4/1962 | Schnell et al. | 260/47 |
| 3,207,794 | 9/1965 | Haines | 568/727 |
| 3,340,310 | 9/1967 | Gilbert et al. | 568/726 |
| 3,388,097 | 6/1968 | Cramer | 260/47 |
| 4,117,018 | 9/1978 | Cleveland et al. | 568/726 |
| 4,182,838 | 1/1980 | Mark et al. | 528/202 |

FOREIGN PATENT DOCUMENTS

| | | | |
|---|---|---|---|
| 6407547 | 3/1965 | Netherlands . | |
| 1017988 | 1/1966 | United Kingdom | 568/726 |
| 1029750 | 5/1966 | United Kingdom | 568/726 |
| 1095959 | 12/1967 | United Kingdom | 568/726 |

OTHER PUBLICATIONS

Gevaert-Photo Producten" French Patent Abstract, Pharmaceuticals, Photographic" French 5/21/65 Indian 22 and 29.5.65 vol. 5, No. 25 FR. 84976/1,285,486.
Korshak et al., "Chem. Abstract" vol. 64 (1966) 6766e.
Korshak et al., "Chem. Abstract" vol. 64 (1966) p. 8321h.

*Primary Examiner*—Werren B. Lone
*Attorney, Agent, or Firm*—Martin B. Barancik; William F. Mufatti

[57] ABSTRACT

Phenol reactants and fluorinated aldehydes or fluorinated ketones are reacted in the presence of organic sulfonic acid catalysts to yield fluorinated monophenols and fluorinated diphenols. Fluorinated monophenols can be isolated and reacted with additional phenol reactant in the presence of organic sulfonic acid catalysts to yield asymmetrical, as well as symmetrical, fluorinated diphenols. A preferred organic sulfonic acid catalyst is methanesulfonic acid. The novel fluorinated monophenols have a hydroxy group and a fluorinated aryl radical or fluorinated alkyl radical substituted upon the benzylic carbon atom. The novel fluorinated diphenols have at least one fluorinated aryl radical or fluorinated alkyl radical substituted upon the methylene carbon atom of the bisphenol.

20 Claims, No Drawings

FLUORINATED MONOPHENOLS AND DIPHENOLS AND METHOD FOR THEIR PREPARATION

This invention relates to an improved method of making monophenols and diphenols having fluorinated alkyl groups and the fluorinated compositions made therefrom.

BACKGROUND OF THE INVENTION

Diphenols, otherwise known as bisphenols, are well-known in the art and are commonly used in the preparation of polycarbonates, polyesters, polyester-carbonate copolymers and other polymers and copolymers. It is well-known that by varying the structures of the monomers used to make the foregoing polymers and copolymers, substantial changes in various properties can be realized, such as changes in impact strength, toughness, transparency, heat distortion limits, dimensional stability, creep resistance, flame-retardancy and the like. It is also desirable to improve such properties, where possible, by changing or altering the structure of monomers used in the polymers or copolymers, and accordingly, it is desirable to provide new and improved monomers to improve the properties of the resultant polymers. Polycarbonate compositions having improved flame-retardance are disclosed in U.S. Pat. No. 4,182,838 where halogenated vinylidene diphenols are used to prepare high molecular weight aromatic polycarbonates. Other halogenated polycarbonates have also been obtained by using halogenated monomers as the main polymer building block. Examples of such polycarbonate compositions include those derived from tetrabromobisphenol-A and tetrachlorobisphenol-A monomers as disclosed in U.S. Pat. No. 3,028,365.

Fluorine-containing polyarylates are described in a paper published in Izvestiya Akademii Nauk SSSR, Seriya Khimicheskaya, No. 9, pp. 1649-1654, September 1965, (Chemical Abstracts 64, 8321h (1966). Homogeneous and mixed terephthalic, isophthalic, and the like, polyesters of 4,4'-(hexafluoroisopropylidene)diphenol monomer and of 4,4'-[alpha-(trifluoromethyl)-benzylidene]diphenol monomer were synthesized, and it was found that the replacement of CH$_3$ groups on the central carbon atom of the isopropylidene diphenol and the methylene diphenol by CF$_3$ groups leads to a lowering of the softening points of homogeneous and mixed polyesters based thereon. Similar monomers are described in Netherlands patent application No. 6,407,548 filed July 2, 1964, and opened for inspection on Jan. 4, 1965. The Netherlands disclosure relates to a process for the preparation of polycarbonate resin by reacting phosgene with 2,2-bis(p-hydroxyphenyl)-1,1,3,3-tetrafluoro-1,3-dichloropropane monomer. The polycarbonate resin was characterized as having very good thermal stability and low vapor permeability. The monomers in the foregoing references were prepared from the corresponding phenol, and in all cases, the positions on the central carbon atom of the diphenol have been substituted with trifluoro- or chlorodifluoro methyl groups or a chlorodifluoro methyl group in combination with a phenyl group.

In U.S. Pat. No. 3,388,097, liquid 4,4'-(1,1,1-trifluoroethylidene)diphenol monomer was made from trifluoroacetaldehyde hydrate and phenol in the presence of anhydrous hydrogen fluoride at 50° C. for 8 hours in a Hastelloy bomb. The liquid product was distilled under reduced pressure at 165°-170° C. and 0.5-0.6 mm. Hg and was obtained in 40% yield. Polyesters were made from these perhaloalkyl bisphenols and specified aromatic acid halides. However, it is noted that the acid catalyst used in making the diphenol is anhydrous hydrogen fluoride; that the reaction is carried out in a "bomb" so as to withstand the considerable autogeneous pressure of anhydrous hydrogen fluoride that exceeds 40 to 150 lbs/in.$^2$ at the required reaction temperatures; and that the reaction product distills at 165-170° C. at reduced pressure. The bisphenols from which the polyesters of U.S. Pat. No. 3,388,097 are made, have the structure:

$$HO-Ar_1-Z-Ar_1-OH \qquad (1)$$

wherein Ar$_1$ is para-phenylene, and Z is a divalent radical having the formula:

$$\begin{array}{c} R \\ | \\ -C- \\ | \\ R \end{array} \qquad (2)$$

wherein R and R' may be the same or different and represent perhalogenated lower alkyl groups, fluorine and chlorine being the preferred halogen species, with the provision that R' may represent hydrogen when R represents a perfluorinated lower alkyl group. In U.S. Pat. No. 3,388,097, it is disclosed that these bisphenols or diphenols are prepared by the acid catalyzed condensation of an appropriate halogenated ketone or aldehyde with two molecules of an appropriate phenol. However, as disclosed above, the acid was hydrogen fluoride gas, and there is no suggestion of solid fluorinated diphenols, or of polycarbonates, or of improved flame retardance of the polyesters derived from the fluorinated diphenols or of a non-pressurized, liquid organic acid catalyst system.

Other halogenated diphenols are disclosed in U.S. Pat. No. 2,435,014 and are obtained by condensing two moles of a t,t-octyl-phenol or -naphthol with 1 mole of a polyhalogenated carbonyl compound, and the condensing agents are a mixture of concentrated sulfuric acid-acetic acid and hydrogen chloride-acetic acid. The polyhalogenated carbonyl compounds claimed in making the condensation products in U.S. Pat. No. 2,435,014 are chlorine, bromine or iodine and the examples illustrate chlorine only as a substituent.

Various organic sulfonic acids are also well-known in the art. In "The Condensed Chemical Dictionary" 8th edition, Van Nostrand Reinhold Company, N.Y. (1971), it is disclosed at page 101 that benzenesulfonic acid is used for making phenol, resorcinol, for other organic syntheses and as catalyst, and at page 776 that methanesulfonic acid is used as a catalyst in polymerization, alkylation and esterification reactions. However, there is no disclosure that the organic sulfonic acids can be used in reactions with fluorinated ketones or fluorinated aldehydes and phenols to produce fluorinated products therefrom.

SUMMARY OF THE INVENTION

Accordingly, it is the primary object of the present invention to provide a novel process for making very pure fluorinated monophenols and diphenols.

It is another object of this invention to provide a non-pressurized acid catalyst system for the preparation of fluorinated monophenols and diphenols from a phenol and a fluorinated aldehyde or a fluorinated ketone compound.

Still another object of this invention is to provide fluorinated monophenols and fluorinated bisphenols having a fluorinated alkyl or a fluorinated aryl group upon the methylene carbon atom of the bisphenol or upon the benzylidene carbon atom of the monophenol.

Another object of this invention is to provide a method of making a diphenol having two different phenol groups.

It is another object of this invention to provide unsymmetrical diphenols having two different phenol groups.

It has now been found that monophenols and diphenols or bisphenols can be made by reacting a phenol reactant and a fluorinated precursor selected from the group consisting of a fluorinated aldehyde and a fluorinated ketone in the presence of an organic sulfonic acid catalyst. The organic sulfonic acid catalysts may be liquids or solids, and the reaction is carried out without the need for pressure vessels. Temperature can be easily controlled and regulated in the reaction, and generally, the temperatures can be substantially varied without the use of a closed vessel or system. In one aspect of the invention, fluorinated diphenols having unsymmetrical phenol groups are made by reacting a first phenol reactant and a fluorinated aldehyde or ketone in the presence of an organic sulfonic acid catalyst to produce a fluorinated monophenol, and thereafter reacting the fluorinated monophenol with a second phenol reactant in the presence of an organic sulfonic acid catalyst to produce a fluorinated diphenol, the first phenol reactant and the second phenol reactant having differing substitution groups thereon.

In another aspect of the present invention, there is provided a fluorinated monophenol having the general formula:

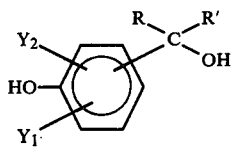
(3)

wherein $Y_1$ and $Y_2$ are each independently selected from the group consisting of hydrogen, chlorine, bromine and alkyl radical having from one to about four carbon atoms; R is selected from the group consisting of fluorinated alkyl radical and fluorinated aryl radical; and R' is selected from the group consisting of fluorinated alkyl radical, fluorinated aryl radical, alkyl radical, aryl radical and hydrogen. The fluorinated monophenols of the present invention have at least one fluorinated alkyl radical or fluorinated aryl radical and a hydroxy group upon the benzylic carbon atom of the fluorinated monophenol.

In accordance with another aspect of the present invention, there is also provided a fluorinated diphenol having the general formula:

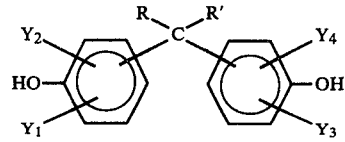
(4)

wherein R is selected from the group consisting of fluorinated alkyl radical and fluorinated aryl radical; R' is selected from the group consisting of fluorinated alkyl radical, fluorinated aryl radical, alkyl radical, aryl radical and hydrogen; and $Y_1$, $Y_2$, $Y_3$, $Y_4$ are substituted upon the respective phenol groups and are each independently selected from the group consisting of hydrogen, chlorine, bromine and alkyl radical having from one to about 4 carbon atoms; with the proviso that when R and R' are both fluorinated alkyl radicals and when R is fluorinated alkyl radical and R' is hydrogen, the phenol group having $Y_1$ and $Y_2$ thereon differs from the phenol group having $Y_3$ and $Y_4$ thereon, and thereby forms a fluorinated diphenol having asymmetrical phenol groups. Accordingly, in one aspect of the present invention, asymmetrical fluorinated diphenols are formed wherein the first phenol group having $Y_1$ and $Y_2$ thereon, differs from the second phenol group having $Y_3$ and $Y_4$ thereon, and thereby forms a fluorinated diphenol having asymmetrical phenol groups.

When R and/or R' are fluorinated alkyl radicals, the alkyl radical is preferably 1 to about 22 carbon atoms, and when R and/or R' is a fluorinated aryl radical, the aryl radical is preferably from 6 to 16 carbon atoms. The phenol reactant must have at least one replaceably aromatic hydrogen atom. When R' is an alkyl radical, the preferred alkyl has from 1 to about 22 carbon atoms, and when R' is an aryl radical, the preferred aryl has from 6 to about 16 carbon atoms. In certain preferred embodiments, R and/or R' is a perfluorinated alkyl radical or a perfluorinated aryl radical or a combination thereof.

In the process of the present invention, the phenol reactant is defined as phenol itself as well as alkyl, chlorine and/or bromine derivatives of phenol, and the alkyl group of the substituted phenol may have from 1 to about 4 carbon atoms.

By the process of the present invention, improvements in the yields of solid diphenol products are obtained by using the organic sulfonic acid catalysts, and the reactions can be carried out in simplified reaction vessels and systems because of the elimination of the necessity for gaseous acid catalysts. Furthermore, by the process of the present invention, it is also possible to produce fluorinated monophenols having a hydroxy-substituted benzylic carbon and at least one fluorinated alkyl or fluorinated aryl group upon the benzylic carbon atom. Asymmetrical fluorinated diphenol or bisphenol products can also be produced by the improved method of the present invention by further reacting the fluorinated monophenol products with a second phenol reactant in the presence of the organic sulfonic acid catalyst, the second phenol reactant having a structure differing from the phenol group of the fluorinated monophenol product, that is, the substituted radicals or groups upon the second phenol reactant must differ from the substituted groups upon the phenol ring of the fluorinated monophenol compound to produce the asymmetrical fluorinated diphenol or bisphenol. Thus, in accordance with the present invention, the fluorinated monophenol compound can be isolated and can be reacted with other phenol reactants to make unsymmetrical or asymmetrical diphenols. By the asymmetry in the fluorinated diphenol molecule, it is possible to maintain polycarbonates and other polymers made from the asymmetrical diphenol, at a better glassy state for a longer period of time, and the polymers are less brittle when the asymmetry is present in the monomer molecule. In another aspect of the present invention, the organic sulfonic acid catalysts permits the use of temperature leverage without a closed vessel, and reactions can be carried out at temperatures up to about 250° C. without vaporization of the acid catalyst even in an open vessel, that is, without the use of a pressurized system or a pressure "bomb".

As used herein, fluorinated monophenol or fluorinated monophenol having a hydroxy-substituted benzylic carbon atom are used interchangeably and are represented by the fluorinated phenol of formula (3). Fluorinated diphenol or fluorinated bisphenol, both symmetrical and asymmetrical are represented by formula (4) wherein the central carbon atom or methylene carbon atom defines the carbon atom position between the two phenol rings and having R and R' attached thereto in formula (4).

In accordance with the present invention, it has been found by gas chromatographic analyses that the fluorinated monophenols and fluorinated diphenols formed by the novel process of this invention, generally have very high purity and are obtained in excellent yields.

DETAILED DESCRIPTION OF THE INVENTION

In certain cases, improved flame retardance is imparted to high molecular weight polymers, such as aromatic polycarbonate resins, by selecting appropriate diphenols to be used with a carbonate precursor in the polymerization reaction. In accordance with the present invention, these diphenols have a fluorinated alkyl radical or a fluorinated aryl radical attached to the central carbon atom, otherwise referred to herein as the methylene carbon atom, positioned between the two phenol rings of the basic bis(hydroxyphenyl) methane structure and derivatives thereof. The present invention also embraces those fluorinated diphenols which are either symmetrical or unsymmetrical relative to the substitution upon the respective phenol rings and as explained in more detail below. The central carbon atom is also substituted with any one of a fluorinated alkyl radical, a fluorinated aryl radical, an alkyl radical, an aryl radical or a hydrogen atom as well as the fluorinated alkyl radical or the fluorinated aryl radical as illustrated in general formula (4) above wherein R, R', $Y_1$, $Y_2$, $Y_3$ and $Y_4$ are each defined above. However, two exceptions apply in the present invention to the foregoing general expression of the fluorinated diphenol formula, namely, when R and R' are both fluorinated alkyl radical or when R is fluorinated alkyl radical and R' is hydrogen, the phenol group or ring, having $Y_1$ and $Y_2$ thereon, differs from the phenol groups having $Y_3$ and $Y_4$ thereon, and thereby forms a fluorinated diphenol having asymmetrical phenol groups. The asymmetry of the two phenol groups in accordance with certain aspects of the present invention is due to the substitution upon the phenol rings, and the asymmetry occurs because of the differences between $Y_1$, $Y_2$, $Y_3$ and or $Y_4$ substituted upon the respective phenol rings. For example, asymmetry results if the substitutions for $Y_1$, $Y_2$, $Y_3$ and $Y_4$ of general formula (4) are as follows:

EXAMPLES OF ASYMMETRICAL FLUORINATED DIPHENOLS

| | $Y_1$ | $Y_2$ | $Y_3$ | $Y_4$ |
|---|---|---|---|---|
| 1. | Cl | H | H | H |
| 2. | CH$_3$ | CH$_3$ | H | H |
| 3. | CH$_3$ | H | Cl | H |
| 4. | CH$_3$ | CH$_3$ | H | Cl |
| 5. | Cl | Cl | H | H |
| 6. | Cl | Cl | Cl | H |
| 7. | CH$_3$ | H | H | H |
| 8. | CH$_3$ | CH$_3$ | C$_2$H$_5$ | C$_2$H$_5$ |
| 9. | CH$_3$ | CH$_3$ | CH$_3$ | Cl |
| 10. | C$_3$H$_7$ | Cl | Cl | Cl |
| 11. | Br | Br | Cl | Cl |
| 12. | CH$_3$ | Cl | Br | Br |

It is readily apparent from the foregoing table that many other combinations of $Y_1$, $Y_2$, $Y_3$ and $Y_4$ in formula (4) are possible, and the asymmetry in formula (4) is possible because of the process of the present invention where the fluorinated monophenol is isolated and thereafter reacted with a second phenol reactant in the presence of an organic sulfonic acid catalyst to produce a fluorinated diphenol, the second phenol reactant having different groups substituted thereon and/or the same groups substituted in different positions thereon, than the phenol ring of the fluorinated diphenol. As used herein, the phrase "having differing substitution thereon" includes different substituted groups, the same groups substituted in different positions upon the respective phenol rings and any other combination which renders the respective phenol rings different from each other and thereby unsymmetrical with respect to each other. In the case of the asymmetrical fluorinated diphenols, not only is it possible to make polymers derived therefrom, for example, polycarbonates, having improved flame retardance due to the fluorinated alkyl group or groups in the monomer, but it is also possible to improve the flexibility of the polymers and to maintain a better glassy state for a greater period of time in polymers derived from the asymmetrical fluorinated diphenols. In preferred embodiments, the fluorinated alkyl group represented by R or R' in the diphenol is from about 1 to about 22 carbon atoms and may be partially fluorinated or completely fluorinated (perfluorinated alkyl group). When any one or all of the positions designated by $Y_1$, $Y_2$, $Y_3$ and $Y_4$ are alkyl radicals in peferred embodiments, the alkyl radicals have from about 1 to about 4 carbon atoms. Furthermore, the alkyl radicals represented by R, R', $Y_1$, $Y_2$, $Y_3$ and $Y_4$ in the diphenol may be straight chain or branched chains or mixtures thereof. When R or R' is a fluorinated aryl group, the aromatic substituent may contain from 6 to about 16 carbon atoms, and one or all of the hydrogen atoms may be replaced by fluorine.

It will be noted that the methylene carbon atom positioned between the two phenol rings may have one hydrogen atom or a small alkyl group and the like thereon, and consequently, there is little or no steric hindrance in the molecule around the central carbon atom in certain cases. Therefore, various position isomers of the fluorinated diphenol structures or mixtures thereof can be made in accordance with the present invention from the phenol reactants, including phenol and the phenol derivatives, and the fluorinated aldehyde or fluorinated ketone compound or from the fluorinated monophenol and a phenol reactant. Thus, while all positional isomers of the fluorinated diphenols of formula (4) are possible, in most cases the isomers are mainly ortho and para, that is, the hydroxy groups are in the ortho and para positions relative to the methylene carbon atom positioned between the two phenol ring structures. In the most preferred embodiments, the isomer is a para, para' isomer when the diphenol monomer is used in conjunction with carbonate and ester precursors and/or other monomers to make polymers or copolymers.

Typical examples of symmetrical fluorinated diphenols which may be made by the process of the present invention include for example, 4,4'-(1-methyltrifluorethylidene)bisphenol, 4,4'-(1-methyldifluoroethylidene)bisphenol, 4,4'-(1-ethylpentafluoropropylidene)diphenol, 4,4'-(1-trifluoromethyltrifluoroethylidene)diphenol, 4,4'-(1-phenyltrifluoroethylidene)bis(2,6-dimethylphenol), 4,4'-(1-methylperfluorooctylidene)diphenol, 4,4'-(1-pentafluorophenylperfluorodecylidene)diphenol, 4,4'-(1-methyltrifluoroethylidene)bis(2,6-dimethylphenol), 4,4'-(1-trifluoromethylpentafluorobenzylidene)bis(2,6-dimethylphenol), and the like wherein the phenol rings are symmetrical. Typical examples of asymmetrical fluorinated diphenols which may be made by the process of the present invention include, for example, 4,4'-(1-trifluoromethyltrifluoroethylidene)-2,6-dimethylbisphenol, 4,4'-(1-methyltrifluoroethylidene)-2'-methyl-2,6-dimethylbisphenol, 4,4'-(1-pentafluoroethylpentafluorobenzylidene)-2-methyl-6-chloro-2',6'-dimethylbisphenol, 4,4'-(1-phenyltrifluoroethylidene)-2-chlorobisphenol, and the like wherein the phenol rings are asymmetrical. The foregoing symmetrical and asymmetrical fluorinated diphenols include various combinations of fluorinated alkyl groups ranging from 1 to about 22 carbon atoms, wherein R and/or R' in formula (4) represents from 1 to about 22 carbon atoms; various combinations of fluorinated aryl groups ranging from 6 to about 16 carbon atoms, wherein R and/or R' in formula (4) represents from 6 to about 16 carbon atoms; various combinations of alkyl groups ranging from 1 to about 22 carbon atoms, wherein R' in formula (4) represents from 1 to about 22 carbon atoms; various combinations of aryl groups ranging from 6 to about 16 carbon atoms, wherein R' in formula (4) represents from 6 to about 16 carbon atoms; and various combinations of substituted chlorine, bromine, and alkyl radicals having from 1 to about 4 carbon atoms upon the phenol rings including unsubstituted phenol, wherein any one of $Y_1$, $Y_2$, $Y_3$ and $Y_4$ in formula (4) can be hydrogen, chlorine, bromine and alkyl radical having from 1 to about 4 carbon atoms. In the diphenols, the complete fluorinated alkyl group is about 2 to about 23 carbon atoms, and the complete aryl group is about 7 to about 16 carbon atoms when the methylene carbon atom located between the phenol rings is included in the alkyl or aryl group. Most of the fluorinated diphenols of the present invention are solids at room temperature and are prepared by reacting, combining or mixing the appropriate phenol reactant with the appropriate fluorinated aldehyde or fluorinated ketone compound in the presence of a catalytic amount of an organic sulfonic acid catalyst, or by reacting, combining or mixing the appropriate monophenol with the appropriate phenol reactant in the presence of a catalytic amount of an organic sulfonic acid catalyst.

The present invention is also directed to making fluorinated monophenols having the structure of formula (3) above by reacting, combining or mixing a phenol reactant and a fluorinated ketone or aldehyde in the presence of an organic sulfonic acid catalyst. Thus, the various embodiments of the present invention include (a) making fluorinated monophenols by reacting, combining or mixing a phenol reactant and a fluorinated ketone or aldehyde in the presence of an organic sulfonic acid catalyst or (b) making fluorinated diphenols by reacting, combining or mixing a phenol reactant and a fluorinated aldehyde in the presence of an organic sulfonic acid catalyst. One key factor in preparing the asymmetrical fluorinated diphenols of the present invention is the fact that the fluorinated monophenols can be isolated from the reaction mixture of a phenol reactant and a fluorinated ketone or aldehyde in the presence of the organic sulfonic acid catalyst. As noted above, the fluorinated ketone or aldehyde and a phenol reactant can produce either a fluorinated monophenol and/or a fluorinated diphenol in the presence of the liquid organic sulfonic acid catalyst system. The particular product depends upon the reaction temperature, length of time of reaction and/or concentration of organic sulfonic acid.

The organic sulfonic acid catalyst allows excellent temperature regulation because the organic sulfonic acids having relatively high boiling points, and they can generally be heated up to about 250° C. without vaporization, depending upon the specific organic sulfonic acid being used as catalyst. Furthermore, they can be used below room temperature, and in certain preferred embodiments, temperatures ranging from about 0° C. to about 250° C. can be used with the liquid organic sulfonic acid catalyst systems. Because of these broad temperature limits, precise temperature regulation or control is possible. The progress of the reaction can be monitored, and the reaction can be terminated at the point in time when the desired product is obtained. Samples of the reaction mixture can be analyzed, for example, by vapor phase chromatography, NMR and the like, and it can be determined if the desired fluorinated monophenol or fluorinated diphenol has been obtained without undue experimentation. Precise temperatures and precise reaction time can be specified only for specific reactants, specific amounts of the reactants and the particular amount of the specific organic sulfonic acid used in the reaction, and based upon the present teachings, one skilled in the art can readily determine these parameters for the specific product desired without undue experimentation by controlling the temperature for a sufficient length of time and/or by controlling the amount or concentration of organic sulfonic acid to produce the desired fluorinated monophenol or fluorinated diphenol. Specific examples below illustrate various temperatures and reaction times. Generally, in preferred embodiments, the reaction time varies from about 0.5 hour up to about 6 or more hours. As will be apparent to one skilled in the art, if the reaction is carried out, for example, at from about 0° C. to about 10° C., it will take a substantially longer period of time to complete the reaction than in the case where the reaction with identical ingredients is carried out at between about 90° C. and 100° C. Generally, monophenols are produced in the reaction when milder reaction conditions are used, such as, when the temperature is about 0° C. to about 150° C. Diphenols are generally produced under more drastic reaction conditions.

The fluorinated diphenols having unsymmetrical phenol groups as shown in formula (3) above, are made by reacting a first phenol reactant and a fluorinated ketone in the presence of an organic sulfonic acid catalyst to produce a fluorinated monophenol, and thereafter reacting the fluorinated monophenol with a second phenol reactant in the presence of an organic sulfonic acid catalyst to produce a fluorinated diphenol, the first phenol reactant and the second phenol reactant having differing substitution groups thereon. This reaction, as well as the reaction for making fluorinated diphenols by reacting, combining or mixing a phenol reactant and a fluorinated aldehyde or ketone in the presence of an organic sulfonic acid catalyst is preferably carried out at temperatures from about 0° C. to about 250° C. for a sufficient amount of time to produce the desired product as indicated above.

The fluorinated monophenol of formula (3) above wherein $Y_1$, $Y_2$, R and R' are defined above, contains a hydroxy (OH) substituted upon the benzylic carbon atom. The same limitations and various combinations for $Y_1$, $Y_2$, R and R' apply to the fluorinated monophenol as to the fluorinated diphenol and are the same limitations and combinations as discussed above for the fluorinated diphenols.

The fluorinated aldehydes and fluorinated ketones are commercially available in various forms, and any of the known forms of the aldehydes and ketones can be used in the processes of the present invention. Any form of the fluorinated aldehyde may be used in the process of the present invention including the free form of the aldehyde, the aldehyde hydrate, the hemiacetal form of the aldehyde, the acetal form of the aldehyde, the trimer form of the aldehyde, the tetramer form of the aldehyde, the cyclic form of the aldehyde, the open chain form of the aldehyde, and the like. Furthermore, any form of the fluorinated ketone may be used in the process of the present invention including the free form of the ketone, the ketone hydrate, the ketal form of the ketone, the hemiketal form of the ketone, the cyclic oligomer form of the ketone, the linear oligomer of the ketone, and the like. The particular form of the aldehyde or the ketone may be chosen, depending upon the desired end product, that is, the desired fluorinated monophenol or the desired fluorinated diphenol.

Examples of the fluorinated aldehyde compound include perfluoroacetaldehyde, perfluoropropionaldehyde, perfluorobutylaldehyde, perfluorooctyanaldehyde, perfluorobenzaldehyde, or any of the partially or completely fluorinated alkyl aldehydes, straight chain or branched, having from 2 to about 23 carbon atoms or any of the partially or completely fluorinated aryl aldehydes having from 7 to about 17 carbon atoms. Examples of the fluorinated ketone compound include hexafluoroacetone, 1,2-dichlorotetrafluoroacetone, 1,1,1-trifluoroacetone, or any of the partially or completely fluorinated ketones, straight chain or branched, having from 3 to about 23 carbon atoms or any of the partially or completely fluorinated aryl ketones having from about 8 to about 18 carbon atoms in the aryl group or groups upon the ketone. As can be seen from the foregoing listed ketones, and applicable also to the aldehydes, the alkyl groups and the aryl groups upon the aldehydes and ketones can be substituted with various other groups and atoms including such halogen groups as chlorine, bromine and fluorine. Thus, R' in formulas (3) and (4) above can have substituted alkyl radicals, substituted aryl radicals and substituted fluorinated alkyl radicals and substituted fluorinated aryl radicals, and in most preferred embodiments, when such radicals are substituted, the substituted group is a halogen group, such as chlorine and/or bromine.

In preferred embodiments, an excess of the phenol reactant is used in the reaction mixture. A ratio of phenol reactant to aldehyde or ketone is not critical as long as there is a sufficient amount of the phenol reactant to react with the fluorinated aldehyde or the fluorinated ketone to provide the fluorinated monophenols or the fluorinated diphenols. The preferred fluorinated aldehyde or fluorinated ketone compounds are generally the perfluorinated aldehyde or perfluorinated ketone compounds. In preferred embodiments, about 1 to about 10 molar quantities of the phenol reactant is used for every mole of the fluorinated aldehyde or fluorinated ketone compound. When a diphenol is prepared from the monophenol, a second phenol reactant in excess of the phenol reactant is also generally used in the reaction mixture, and from about 1 to about 10 molar quantities of the phenol reactant are used per molar quantity of the monophenol reactant.

Any appropriate phenol reactant may be used in accordance with the present invention including phenol, substituted phenol or any phenol derivative as long as there is at least one replaceable aromatic hydrogen atom thereon. As used herein phenol, phenol reactant and phenol compound are used interchangeably and include any appropriate phenol, substituted phenol or phenol derivative. The preferred phenol reactant is generally phenol itself. Other phenols include, for example, o-cresol, 2,6-xylenol, 6-chloroorthocresol, orthochlorophenol, or any phenol compound substituted with alkyl radicals having preferably from about 1 to about 4 carbon atoms, chlorine or bromine and having at least one replaceable hydrogen atom on the ring. As indicated above, when an asymmetrical diphenol is produced from a monophenol and a phenol compound in the presence of the organic sulfonic acid catalyst, the second phenol ring differs from the phenol ring upon the monophenol so that there is asymmetry in the resulting diphenol. Symmetrical diphenols can also be made from the monophenol and a second phenol compound in the presence of the organic sulfonic acid when the phenol rings are the same.

In accordance with the present invention, the acid catalyst system is limited to organic sulfonic acids. Pressure, pressure bombs and pressure vessels are not necessary in the process of the present invention and the reaction process steps can be carried out at atmospheric pressure without the necessity of pressure or pressurized vessels. Organic sulfonic acids are well-known in the prior art and are available commercially, and generally when organic sulfonic acids are used as the acid catalyst systems in the processes of the present invention, relatively high yields of high purity solid fluorinated monophenols and solid fluorinated diphenols are obtained from the reaction of phenol compounds and fluorinated aldehyde and fluorinated ketone compounds.

The organic sulfonic acid catalyst which may be used in the processes of the present invention, include methanesulfonic acid, ethanesulfonic acid, propanesulfonic acid, butanesulfonic acid, and various other straight-chained and branched-chain alkyl sulfonic acids having up to about 10 carbon atoms, and various aryl sulfonic acids, including, benzenesulfonic acid, trichlorobenzenesulfonic acid, toluenesulfonic acid, and the like. Any organic sulfonic acid may be used in accordance with the present invention as long as it is liquid at the particular reaction temperature and as long as it does not adversely affect the combination of the fluorinated aldehydes or fluorinated ketones with phenol compounds or the combination of a monophenol and phenol reactant.

Although external heat is not required in the reaction of the phenol compound and the fluorinated aldehyde compound or the fluorinated ketone compound to produce the solid fluorinated monophenols or diphenols in the presence of the liquid organic sulfonic acid catalyst or in the reaction of the fluorinated monophenol and the phenol compound to produce the solid fluorinated asymmetrical diphenols in the presence of the liquid organic sulfonic acid catalyst, it is preferred to heat the reaction mixture above ambient up to about 250° C., depending upon the nature of the acid catalyst and the respective aldehydes and ketones. Optimum temperatures are generally about 0° C. to about 150° C. for the preparation of monophenols. The organic sulfonic acid catalyst material is present in a catalytic amount, however, the amount of acid catalyst is generally an amount which saturates the phenol or ketone and/or the reaction mixture in which water and/or alcohol are formed during the reaction. In preferred embodiments, the organic sulfonic acid catalysts are available in amounts varying from about 1 weight percent to about 50 weight percent based upon the weight of the phenol reactant. Although the organic sulfonic acid catalysts are generally anhydrous so that they will not introduce water into the reaction mixture, it is to be understood that water and/or alcohol are formed in the condensation reaction leading to monophenols and diphenols depending upon the nature of the aldehyde or ketone precursor employed.

It is also possible to use co-catalysts, such as, mercaptans and other sulfhydryl-containing compounds, with the acid catalyst to speed up the proton-catalyzed reaction. Optional steps include separation of the isomers, for example, by recrystallization, by distillation or by solvent separation techniques to separate the o,o'- and o,p'- from the p,p'-isomers.

The chlorination or bromination of the fluorinated diphenol or fluorinated monophenol may be carried out before the diphenol or monophenol is formed or after the diphenol or monophenol is formed by conventional halogenation techniques when the chlorine or bromine derivatives of the fluorinated bisphenol or fluorinated monophenols are desired. For example, the phenol compound or compounds used to make the diphenols or monophenols may contain the chlorine or bromine radicals or mixtures thereof before reaction with the appropriate fluorinated aldehyde or ketone, or the bromine or chlorine radicals or mixtures thereof may be be placed upon the fluorinated diphenol or fluorinated monophenol after it has been synthesized from the phenol compound (or monophenol) and the appropriate fluorinated aldehyde or ketone. When alkyl derivatives of the fluorinated diphenols are desired, they are best prepared from the corresponding alkylphenol precursors, such as, o-cresol, 2,6-xylenol, o-isopropylphenol, o-tertiary-butylphenol, 2-chloro-6-methylphenol and the like.

The following specific examples describe the novel diphenol and monophenol compositions and the novel processes of making the diphenol and monophenol compositions including asymmetrical diphenols of the present invention. They are intended for illustrative purposes only and should not be construed as a limitation.

EXAMPLE 1

Preparation of 2,6-dimethyl-4(1-hydroxy-1-trifluoromethyl-2,2,2-trifluoroethyl)phenol

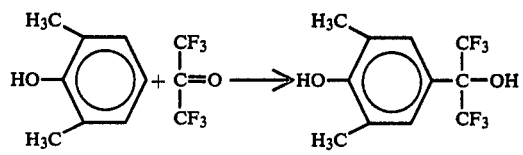

To a mixture of 610 g (5.0 moles) of 2,6-xylenol and 100 g of methanesulfonic acid, placed into a 3-neck, 1-liter flask, equipped with a mechanical stirrer, thermometer, addition funnel and dry-ice condenser, protected from atmospheric moisture by nitrogen flow, there was added gradually, with good stirring, 96.5 g (0.5 mole) of hexafluoroacetone-sesquihydrate, while maintaining the temperature of the contents of the flask between 94° and 100° C. After the completion of the addition in about 70 minutes, the red colored reaction mixture was kept at 100° C. for an additional period of 4.5 hrs., at the end of which time gas chromatographic analysis indicated that the reaction was essentially complete. The entire mixture was then dissolved in methylene chloride; the solution was washed with water until acid-free; the solvent was stripped-off; and the residue was distilled in water aspirator vacuum until all of the unreacted 2,6-xylenol was removed by distillation. The pot residue was dissolved in methylene chloride, treated with charcoal and filtered. Upon cooling, white crystals formed in the pale yellow solution. The crystals were isolated by filtration and were analyzed by gas chromatography which indicated that they were 99.5% pure, and that they were 2,6-dimethyl-4(1-hydroxy-1-trifluoromethyl-2,2,2-trifluoroethyl)phenol. The melting point of the crystals was 82°-83° C. The yield of the product was better than 90% of the theory.

EXAMPLE 2

Preparation of 2-methyl-4(1-hydroxy-1-trifluoromethyl-2,2,2-trifluoroethyl)phenol

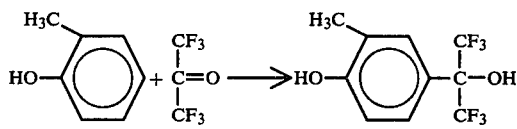

The procedure of Example 1 was essentially repeated, except that the xylenol was replaced with 540 g (5.0 moles) of orthocresol, and gaseous hexafluoroacetone, 83 g (0.5 mole) was added via a glass gas delivery tube reaching below the surface of the well-stirred mixture. At the completion of the reaction, as in Example 1, after recrystallization from hexane, white crystals of 1-methyl-4(1-hydroxy-1-trifluoromethyl-2,2,2-trifluoroethyl)phenol having 99.7% purity and melting at 89.5°-90.5° C. were isolated from the reaction mixture.

EXAMPLE 3

Preparation of 2,6-dimethyl-4(1-hydroxy-1(chlorodifluoromethyl)-2-chloro-2,2-difluoroethyl)phenol

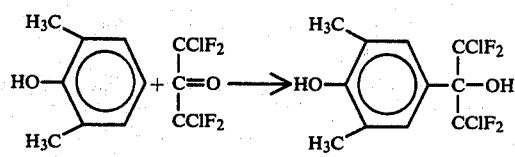

The procedure of Example 1 was repeated with 99.5 g (0.5 mole) of 1,2-dichlorotetrafluoroacetone in place of the hexafluoroacetone hydrate. Recrystallization of the pot residue from hexane, after the removal of the unreacted 2,6-xylenol by distillation, yielded white crystals of 2,6-dimethyl-4(1-hydroxy-1(chlorodifluoromethyl)-2-chloro-2,2-difluoroethyl)phenol having 99.2% purity (as analyzed by gas chromatography) and melting at 90.5°–92° C. The yield was essentially quantitative.

EXAMPLE 4

Preparation of 4,4'-(1-trifluoromethyltrifluoroethylidene)bis(2,6-dimethylphenol)

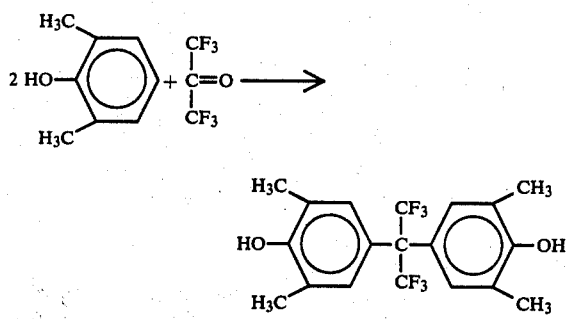

Repeating exactly the procedure of Example 1, except that the temperature was elevated to 160° C., yielded, after cooling, a reaction mass which was extracted with water and methylene chloride to yield a solid residue. After washing with methylene chloride, the solid residue yielded pure-white crystals melting at 218° to 219° C. and having a purity of 99.7%. The methylene chloride extract was stripped of the solvent, and excess xylenol yielded a slightly orange residue, which after washing by cyclohexane, produced white crystals, shown by gas chromatography to be 4,4'-(1-trifluoromethyltrifluoroethylidene)bis(2,6-dimethylphenol). The yield was nearly quantitative.

EXAMPLE 5

Preparation of 4,4'-(1-methyltrifluoroethylidene)bis(2,6-dimethylphenol)

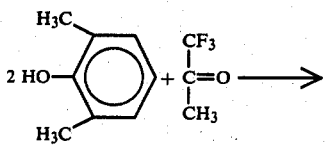

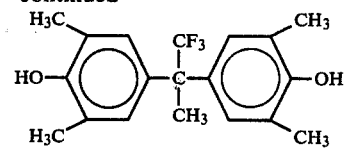

When the procedure of Example 2 was repeated with 610 g (5 moles) of 2,6-xylenol in place of the o-cresol and 53.0 g (0.5 mole) of gaseous 1,1,1-trifluoroacetone in place of the hexafluoroacetone, the reaction product at 100° C. consisted entirely of 4,4'-(1-methyltrifluoroethylidene)bis(2,6-dimethylphenol), which was isolated by filtration of the slightly warm reaction slurry at the termination of the reaction. After washing with methylene chloride the white crystals melted at 201° to 202.5° C. and had a purity of 98.6%. The structure of the compound was confirmed by proton nmr run in deuterioacetone, which displayed the central methyl at 1.83, the xylyl methyls at 2.20, the aromatic protons at 6.87 and the hydroxylic protons at 7.2 ppm downfield from the TMS reference.

EXAMPLE 6

Preparation of 4,4'-(1-methyltrifluoroethylidene)bisphenol

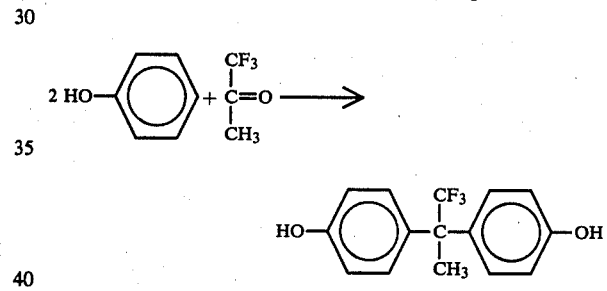

Repeating the process of Example 5 using 470 g (5 moles) of phenol in place of the xylenol, yielded a reaction mixture consisting of 66% of 4,4-(1-methyltrifluoroethylidene)bisphenol and 34% of 2,4'-(1-methyltrifluoroethylidene)bisphenol. After the removal of excess phenol by distillation, the mixture of the two isomers was readily separated by elution chromatography over silica, using methylene chloride as eluant. After the emergence of the 2,4'-isomer, the 4,4'-isomer was eluted. The 4,4'-isomer crystallized out readily from the concentrated solution in the form of white crystals which melted at 93°–94.5° C. and had a purity of 98.2%.

EXAMPLE 7

Preparation of 4,4'-(1-trifluoromethyltrifluoroethylidene)-2,6-dimethylbisphenol

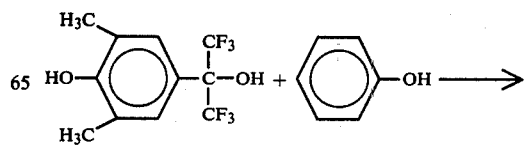

-continued

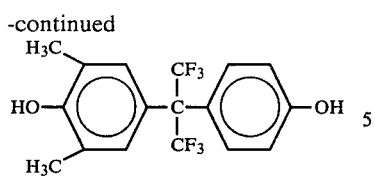

Into the reaction flask described in Example 1 was charged 108.8 g (0.4 mole) of the isolated monophenol reaction product of Example 1 having a melting point 82°-83° C., together with 374 g (4.0 moles) of phenol and 100 g of benzenesulfonic acid. The reactants were heated to 155° C. for a period of 6 hours. The reaction mixture was washed with water (4 times), and extracted with methylene chloride. This was stripped of the solvent and excess phenol by distillation and yielded a residue from which white crystals formed. The white crystals, after recrystallation from cyclohexane, had a melting point of 153.5° to 155.5° C. and were of 99.7% purity as determined by gas chromatography. Analysis by proton nmr confirmed the structure of the 4,4′-(1-trifluoromethyltrifluoroethylidene)-2,6-dimethylbisphenol by displaying the methyl peaks at 2.2, the aromatic protons of the xylyl portion of the molecule at 7.0, the phenolic AB quadruplet centered at 6.8 and 7.3, and the hydroxylic protons at 5.0 and 4.7 ppm, respectively, downfield from TMS in deuteriochloroform solution.

EXAMPLE 8

Preparation of 4,4′-(1H-1,1-perfluorooctylidene)bisphenol

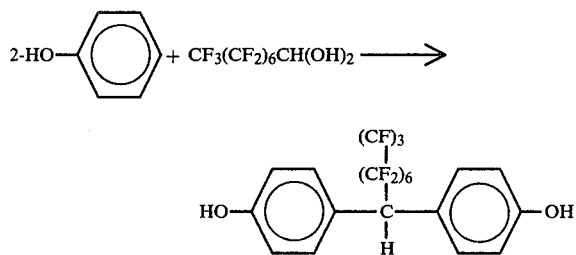

The procedure of Example 1 was followed, except that the 2,6-xylenol was replaced with 470 g (5.0 moles) of phenol and the hexafluoroacetone was replaced wiht 208 g (0.5 mole) of perfluorooctanaldehyde hydrate. After the completion of the addition of the perfluorooctanaldehyde hydrate to the mixture of phenol and methanesulfonic acid, the reaction mixture was kept at 100° C. for a period of 0.5 hour rather than for 4.5 hours as in Example 1. The isolation of the product and recrystallization were carried out as in Example 1. The pure white crystals were identified as 4,4′-(1H-1,1-perfluorooctylidene)bisphenol and had a sharp melting point of 138°-139° C.

EXAMPLE 9

Preparation of 4,4′-(1H-trifluoroethylidene)bisphenol

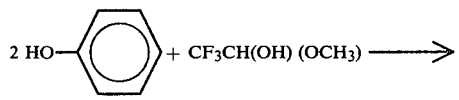

-continued

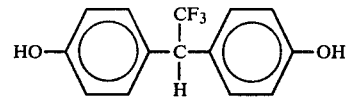

The procedure of Example 8 was followed except that 64.5 g (0.5 mole) of trifluoroacetaldehydr methyl hemiacetal was added to the phenol and methanesulfonic acid instead of the perfluorooctanaldehyde hydrate of Example 8. A crystalline compound having a melting point of 87° C. to 89° C. was isolated and was identified as 4,4′-(1H-trifluoroethylidene(bisphenol.

In the foregoing examples, both monophenols and diphenols have been prepared by reacting a phenol reactant and a fluorinated precursor selected from the group consisting of a fluorinated aldehyde and a fluorinated ketone in the presence of an organic sulfonic acid catalyst. Both symmetrical and asymmetrical diphenols have also been illustrated in the foregoing examples.

Other modifications and variations of the present invention are possible in light of the above disclosure. It is therefore, to be understood, that changes may be made in the particular embodiments described above which are in the full intended scope of the invention as defined in the appended claims.

What is claimed is:

1. A fluorinated monophenol having the general formula:

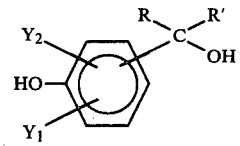

wherein $Y_1$ and $Y_2$ are each independently selected from the group consisting of hydrogen, chlorine, bromine and alkyl radical having from 1 to about 4 carbon atoms; R is selected from the group consisting of fluorinated alkyl radical and fluorinated aryl radical; and R′ is selected from the group consisting of fluorinated alkyl radical, fluorinated aryl radical, alkyl radical, aryl radical and hydrogen.

2. The fluorinated monophenol of claim 1 wherein R is a fluorinated alkyl radical having from 1 to about 22 carbon atoms.

3. The fluorinated monophenol of claim 1 wherein R′ is a fluorinated alkyl radical having from 1 to about 22 carbon atoms.

4. The fluorinated monophenol of claim 1 wherein R is a fluorinated aryl radical having from 6 to about 16 carbon atoms.

5. The fluorinated monophenol of claim 1 wherein R′ is a fluorinated aryl radical having from 6 to about 16 carbon atoms.

6. The fluorinated monophenol of claim 1 wherein R′ is an alkyl radical having from 1 to about 22 carbon atoms.

7. The fluorinated monophenol of claim 1 wherein R′ is an aryl radical having from 6 to about 16 carbon atoms.

8. The fluorinated monophenol of claims 1, 2, or 3 wherein the fluorinated alkyl radical is perfluorinated.

9. The fluorinated monophenol of claims 1, 4, or 5 wherein the fluorinated aryl radical is perfluorinated.

10. The fluorinated monophenol of claim 1 wherein R' is hydrogen.

11. A fluorinated diphenol having the general formula:

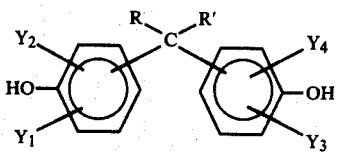

wherein R is selected from the group consisting of fluorinated alkyl radical and fluorinated aryl radical; R' is selected from the group consisting of fluorinated alkyl radical, fluorinated aryl radical, alkyl radical, aryl radical and hydrogen; and $Y_1$, $Y_2$, $Y_3$ and $Y_4$ are substituted upon the respective phenol groups and are each independently selected from the group consisting of hydrogen, chlorine, bromine and alkyl radical having from 1 to about 4 carbon atoms; with the proviso that when R and R' are both fluorinated alkyl radical, and when R is fluorinated alkyl radical and R' is hydrogen, the phenol group having $Y_1$ and $Y_2$ thereon, differs from the phenol group having $Y_3$ and $Y_4$ thereon, and thereby forms a fluorinated diphenol having asymmetrical phenol groups.

12. The fluorinated diphenol of claim 11 wherein R is a fluorinated alkyl radical having from 1 to about 22 carbon atoms.

13. The fluorinated diphenol of claim 11 wherein R' is a fluorinated alkyl radical having from 1 to about 22 carbon atoms.

14. The fluorinated diphenol of claim 11 wherein R is a fluorinated aryl radical having from 6 to about 16 carbon atoms.

15. The fluorinated diphenol of claim 11 wherein R' is a fluorinated aryl radical having from 6 to about 16 carbon atoms.

16. The fluorinated diphenol of claim 11 wherein R' is an alkyl radical having from 1 to about 22 carbon atoms.

17. The fluorinated diphenol of claim 11 wherein R' is an aryl radical having from 6 to about 16 carbon atoms.

18. The fluorinated diphenol of claims 11, 12 or 13 wherein the fluorinated alkyl radical is perfluorinated.

19. The fluorinated diphenol of claims 11, 14 or 15 wherein the fluorinated aryl radical is perfluorinated.

20. The fluorinated diphenol of claim 11 wherein the phenol group having $Y_1$ and $Y_2$ thereon, differs from the phenol group having $Y_3$ and $Y_4$ thereon, and thereby forms a fluorinated diphenol having asymmetrical phenol groups.

* * * * *